US00PP11245P

United States Patent [19]

Newby, Jr. et al.

[11] Patent Number: Plant 11,245

[45] Date of Patent: Feb. 29, 2000

[54] GRAPEVINE CV. SUGRAFOURTEEN

[75] Inventors: Harry Joe Newby, Jr., Mecca; David W. Cain, Bakersfield, both of Calif.

[73] Assignee: Sun World International, Inc., Bakersfield, Calif.

[21] Appl. No.: 08/869,366

[22] Filed: Jun. 5, 1997

[51] Int. Cl.[7] ..... A01H 5/00

[52] U.S. Cl. ..... Plt./205

[58] Field of Search ..... Plt./47.1, 205, Plt./206, 207

[56] References Cited

U.S. PATENT DOCUMENTS

P.P. 3,106 4/1972 Garabedian ..... Plt./207

P.P. 9,865 4/1997 Ralli et al. ..... Plt./47.1

*Primary Examiner*—Howard J. Locker

*Attorney, Agent, or Firm*—Knobbe, Martens Olson & Bear, LLP

[57] ABSTRACT

A new and distinct grapevine variety characterized by its firm, early ripening, naturally large, red berries.

1 Drawing Sheet

BACKGROUND AND SUMMARY OF THE INVENTION

This invention relates to the discovery and asexual propagation of a new variety of grapevine, *Vitis vinifera* cv. Sugrafourteen. The Sugrafourteen variety was discovered on Jun. 26, 1991 by Harry Joe Newby, Jr., in a commercial vineyard designated Sun World Ranch 543 near Thermal, Riverside County, Calif., and was evaluated and asexually propagated by David W. Cain. The variety was discovered as a spontaneous mutation on three canes from two spurs of a vine of *Vitis vinifera* cv. Sugraone, the subject of U.S. Plant Pat. No. 3,106, issued on Apr. 11, 1972. 'Sugraone' is also known in the market place under the name 'Superior Seedless'. The new variety is characterized by producing firm, low acid, early ripening, naturally large, red berries.

The new variety was first asexually propagated by David W. Cain in February 1992, in Wasco, Kern County, Calif., using hardwood cuttings. The Sugrafourteen grapevine maintains its distinguishing characteristics as hereinafter set out through successive asexual propagations using, for example, hardwood cuttings. This variety resembles its parent, Sugraone, being similar in time of bud break, time of ripening, fruit characteristics and vine growth habit. It can be distinguished from Sugraone by its distinct red skin color as opposed to the white skin color of Sugraone. An allelic polymorphism DNA comparison showed Sugrafourteen to be identical with Sugraone for all of the alleles included in the comparison.

The present variety resembles Ralli Seedless (U.S. Plant Pat. No. 9,865) in many respects. Both arose as spontaneous mutations of the Sugraone variety. Based on the patent description of Ralli, the present variety appears to differ from Ralli in possessing no red tinge to the foliage, and having slightly larger clusters of about 1.2 kilograms as compared with 0.5 to 0.75 kilograms for Ralli Seedless. Leaves of Sugrafourteen are indistinguishable from those of Sugraone whereas Ralli's leaves are described as having a more open upper leaf shape. Berries of Sugrafourteen are lighter pink and have more difficulty obtaining full coloration as compared to berries of Ralli Seedless.

Sugrafourteen differs from the commercially available red skin Flame Seedless variety by having distinctly larger, less uniform, and more ovate berry shape. It has lower acidity than Flame Seedless and ripens its fruit earlier.

BRIEF DESCRIPTION OF THE FIGURE

The accompanying drawing in FIG. 1 illustrates, in full color, a typical cluster of berries, stem section, young shoot and mature leaf blade of the new grapevine.

DETAILED BOTANICAL DESCRIPTION OF THE INVENTION

Figure 1:
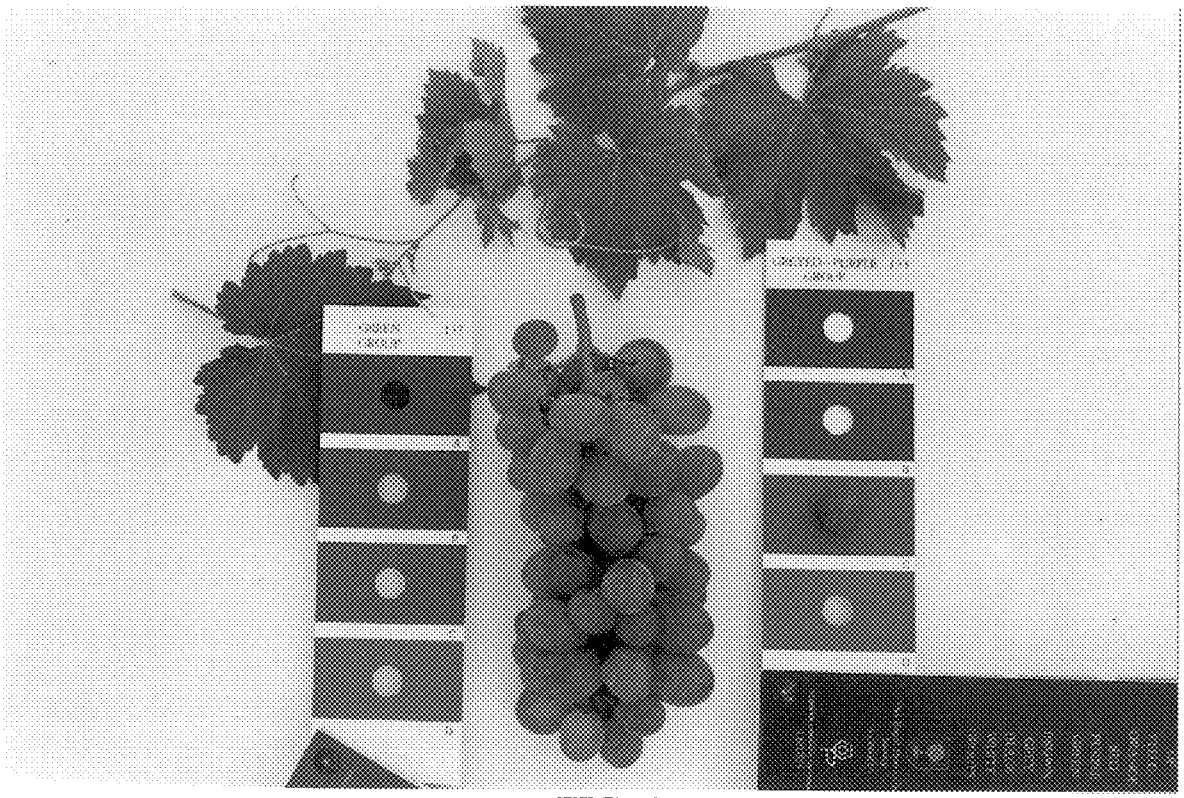

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

The descriptive matter which follows pertains to Sugrafourteen plants grown in the vicinity of Wasco, Kern County, Calif. during 1995 and 1996 and is believed to apply to plants grown under similar conditions of soil and climate elsewhere:

VINE

The vine on its own root is large in size and is vigorous. The foliage is dense, and the vines are of average productivity, yielding approximately 20,000 kg/ha of packable fruit. Yields are equal to or slightly less than Sugraone. The vine requires cane pruning; the basal buds not being sufficiently fruitful to produce commercially acceptable yields.

The trunk is of medium diameter and vigor compared to similar age varieties and the bark exhibits long, split straps. The surface is of medium texture and the inner bark is about Greyed-Orange 174C in color. Mature canes are about 8.6 mm wide at the node. The average distance between nodes is about 163 mm.

CURRENT SEASON SHOOTS

Shoots exhibit strong vigor during flowering. Flowering shoots are semi-drooping when not tied. The dorsal side of both the internodes and nodes is green with red stripes, about Greyed-Purple 183B in color. The ventral side of both the internodes and the nodes is green. Anthocyanin coloration is absent or very weak in the immature shoot buds. Nodes of flowering shoots have very sparse prostrate hairs, while erect hairs are absent.

Young shoot tips are half-open in form. Medium anthocyanin coloration, slightly more intense than Sugraone, is distributed as striped piping in the young shoot tips. Prostrate hairs are present in average densities at the shoot tips, while erect hairs are very sparse or absent at the shoot tips.

Tendrils average about 20 cm in length and are medium thickness, similar to Sugraone, and are discontinuously distributed on the shoot at full flower. Tendrils are about Yellow-Green 145B in color, and are trifurcated in form. Inflorescences are normally produced at nodes 5 to 7 on current season shoot growth.

DORMANT CANES

Woody canes are elliptic in cross section. The surface of woody canes is smooth and about Greyed-Orange 165B in color. Lenticels are absent, and erect hairs are absent or very sparse both at the nodes and in the internodes.

Leaf-producing buds are many, are slightly pointed and of medium size—about 0.4 cm by 0.4 cm. Basal buds are unfruitful; mid-shoot and distal buds are fruitful and seldom dead. Thus, Sugrafourteen vines require cane pruning similar to Sugraone. Bud burst is early, with Sugraone.

LEAVES

In general, the upper surface of a young leaf is about Yellow-Green 144A in color. Prior to flowering, anthocyanin coloration is weak or absent in the distal leaves. On the lower surface of the young leaves, prostate hairs are distributed very sparsely between veins and sparsely on the veins, while erect hairs are absent or very sparse between the veins and are sparse on the veins.

Mature leaves have a generally circular-oval outline and a flat profile. Leaves are of medium thickness and size (about 12.2 cm long and about 15.9 cm wide) and the blades are of medium size, pentagonal in shape and have 3 to 5 lobes. The leaf blade tip lies in the plane of the leaf. The leaf margin shows slight undulation, and the leaf apex is cuspidate. The leaf blade has undulations between the main and lateral veins, but only near the petiole. Teeth are convex on both sides and are of medium length. The upper leaf sinuses are closed. The base of the upper leaf sinuses is V-shaped.

The upper surface of the leaf is about Green 137B in color. Anthocyanin coloration is absent or very weak on the main veins of the upper leaf surface. The upper leaf surface is smooth in texture and has a semi-glossy surface appearance. Erect hairs are absent or very sparse on the veins; prostrate hairs are absent on the veins. Blistering on the upper side surface of the blade is absent or very weak. The blades are goffered. Autumn coloration of the leaves is yellow.

The lower leaf surface is about Green 137D in color, is weak in glossiness and is without pubescence. Anthocyanin coloration of the main veins on the lower leaf surface is weak to medium. The lower leaf surface is smooth in texture and dull in surface appearance. Erect hairs are absent or very sparse on the veins, and prostrate hairs are absent on the veins.

The petiole is shorter than the middle vein: 8.6 cm in length. There are no prostrate or erect hairs present on the petiole. The petiole sinus has slightly overlapping lobes and is V-shaped at the base. There are no particularly distinguishing features with respect to the petiole sinus.

Overall, leaves of Sugrafourteen are indistinguishable from those of Sugraone and lack the red tinge of the leaves of Ralli Seedless as described in its patent description.

FLOWERS

The flowers are of average size, length and shape. The 5th node is the first flowering node. The inflorescence is of average length, about 18 cm. Inflorescences occur with a frequency of up to one per shoot.

In Wasco, Calif., flowers attained first and full bloom at generally the same time as Sugraone, average as compared with most other similar varieties in the growing area of Wasco. Flowers are of medium size and length, usually about 10.2 per cane. Flowers are hermaphroditic.

FRUIT

The fruit of Sugrafourteen ripens early, with Sugraone. It is suitable for fresh market use and has a good shipping quality and medium keeping quality. As is typical of *Vitis vinifera,* the fruit has good resistance to insects and diseases.

Fruit of Sugraone harvested on Jul. 9, 1996 was found to have a solids-sugar content of about 15.8 brix, and about 0.59 g acid. The pH of the juice was about 3.79. Sugrafourteen harvested on the same day was found to have a soluble solids content of 17.3 brix and 0.52 g acid with a pH of 3.91. By Jul. 31, 1996, Sugrafourteen had attained 18.0 brix and 0.44 g acid while Sugraone had 15.4 brix and 0.52 g acid.

The size of the berry clusters (excluding the peduncle) is large, weighing on the average about 1201 grams. The loosely compact, cylindrical-conical cluster usually bears an average of about 231 berries. The cluster is about 26.8 cm long and about 13.9 cm wide. Cluster size is slightly larger than that described for Ralli Seedless.

The peduncle is of average length and shows weak lignification. Peduncle color is about Yellow-Green 145C.

Berries are generally large, variable in size and are of obtuse ovate shape with a circular cross section. On average the longitudinal axis is about 21.9 mm, and the horizontal axis is about 17.4 mm. Single berry weight is on average about 5.2 g. Berries are firm, and about Greyed-Purple 183C in color. Berries are difficult to color and require exposure to sunlight to attain adequate commercial coloration. Sugrafourteen appears to have more difficulty in attaining full coloration as compared with Ralli Seedless and berries appear to have a lighter pink coloration than those of Ralli Seedless. Berries have heavy cuticular wax and a medium pedicel length. Separation of the berry from the pedicel is difficult. The berries have a neutral to faintly muscat flavor when well ripened.

The skin is thick, tough in texture, tenacious to the flesh, and without roughness or reticulation. Berries contain an average of 1.6 small vestigial seeds averaging 9.14 milligrams each, which are not noticeable when the berries are eaten.

What is claimed is:

1. A new and distinct variety of grapevine cv. Sugrafourteen, substantially as herein illustrated and described.

* * * * *